United States Patent
Winter et al.

(12) 
(10) Patent No.: US 6,669,967 B2
(45) Date of Patent: *Dec. 30, 2003

(54) METHOD FOR THE TREATMENT OF SYMPTOMS RELATED TO NORMAL HORMONAL VARIATIONS IN WOMEN

(75) Inventors: Kaj Winter, Copenhage (DK); Christer Hedman, Mölnlycke (SE); Lars Kärnerud, Tenhult (SE)

(73) Assignee: Natumin Pharma AB, Huskvarna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/184,060

(22) Filed: Jun. 28, 2002

(65) Prior Publication Data

US 2003/0161890 A1 Aug. 28, 2003

Related U.S. Application Data

(63) Continuation-in-part of application No. 09/942,967, filed on Aug. 31, 2001.
(60) Provisional application No. 60/229,308, filed on Sep. 1, 2000.

(51) Int. Cl.$^7$ ................................................ A61K 35/78
(52) U.S. Cl. ........................................ 424/725; 424/778
(58) Field of Search ................................ 424/725, 778, 424/539; 549/410; 514/458

(56) References Cited

U.S. PATENT DOCUMENTS 5,569,459 A    10/1996   Shlyankevich

FOREIGN PATENT DOCUMENTS

EP     1 057 483 A1    12/2000

OTHER PUBLICATIONS

Dr. Kaj Winther, "Cognitive Function and Natural Medicines", Paper No. 29, from *Vitafoods International Conference 2000*, May 3–5, 2000, Geneva, Switzerland.

K. Winther et al., "P01.24: Pre–Menstrual Tension is Markedly Reduced by Femal, a Natural Product", from *Maturitas: The European Menopause Journal*, Jun. 2000, vol. 35, suppl. 1.

K. Winther et al., "183: Premenstrual Tension (PMS) Symptoms Such as Weight Gain and Raw Lutheal Phase Score are Reduced by Femal, A Natural Product", from *Nordisk Forening For Obstetrikk Og Gynekologi*, Jun. 2000, Oslo.

K. Winther et al., "A Pollen Pistil Extract, Femal, Reduces Weight Gain, Irritability and Dysphoric Disorders in Women Suffering from Premenstrual Syndrome (PMS)", from *Recent Research in Gynecological Endocrinology*, Dec. 2000, pp. 57–61, New York: The Parthenon Publishing Group.

Femal: Natural help for PMS, http://www.sisuhealth.com/products/Femal.html retrieved Apr. 24, 2001.

Menopause treatment options (continued), http://www-.menopause.org/mgremedies.htm retrieved Apr. 24, 2001.

Primary Examiner—Christopher R. Tate
Assistant Examiner—Patricia Patten
(74) *Attorney, Agent, or Firm*—Browdy and Neimark PLLC

(57) ABSTRACT

A method for the treatment of disorders related to normal hormonal variations in women during fertile, peri- and post-menopausal age, by the administering of a composition comprising, as active ingredients, a water and/or fat-soluble cytosolic extract of pollen and optionally pistils, optionally combined with Royal Jelly and vitamin E.

20 Claims, No Drawings

METHOD FOR THE TREATMENT OF SYMPTOMS RELATED TO NORMAL HORMONAL VARIATIONS IN WOMEN

The present application is a continuation-in-part of copending parent application Ser. No. 09/942,967, filed Aug. 31, 2001, and claims benefit of U.S. provisional application No. 60/229,308, filed Sep. 1, 2000.

FIELD OF THE INVENTION

The invention relates in a first aspect to a method for the treatment of disorders related to normal hormonal variations in women during fertile as well as, peri- and post-menopausal age, by the administering of a composition comprising, as active ingredients, a water- and/or fat-soluble cytosolic extract of pollen and optionally pistils.

The invention, in another aspect, relates to a composition comprising, as active ingredients, a water- and/or fat-soluble cytosolic extract of pollen and optionally pistils for the treatment of disorders relating to normal hormonal variations in women during fertile, as well as peri- and post-menopausal age.

BACKGROUND OF THE INVENTION

Disorders relating to normal variation of the sex hormone cycle of women of fertile age are tension, irritability, dysphoria, abdominal distension or bloatedness, severe breast tension, headache or migraine, edema, weight changes, sleep disturbances etc. The overall well being as well as the social and professional life may be influenced.

Over the years different treatment options have been suggested to be effective for the treatment of the above-mentioned disorders. However few have shown a consistent efficacy on irritability, dysphoria, bloatedness and edema, tension, breast tension, weight gain, headache and sleep disturbances related to normal variations in the sex hormone cycle of women of fertile age. The pharmacological treatments that have been tried include serotonin re-uptake inhibitors, diuretics, hormonal treatment as well as dietary interventions with e.g. vitamin and mineral supplementation, and natural products. Many of the compounds used for the treatment are limited due to adverse effects.

Also menopause, which is caused by a lowering of the production of female sex hormones at the age around 50, can to many women generate disorders such as edema, hot flushes, attacks of sweating, muscle and possibly joint pain, sleep disturbances, dysphoria, nervousness, mood swings, headache, palpitations (enhanced frequency of heart rate), dry mucous membranes and pain during intercourse, urinary disturbances such as stress incontinence, frequent passing water and pain/irritability of the bladder and urethra during the process of passing water etc. All these disorders reflect age related hormonal changes which hitherto only have been alleviated effectively by the administration of female sex hormones like estrogen and the like. However, there are studies showing that hormone therapy may have a carcinogenic effect as a negative side effect.

Four out of five women have disturbing menopause disorders for at least one year and 25% of women have menopause disorders for more than 5 years. Half of all women have severe disorders and a population of 5 million inhabitants will constantly include about 200,000 women in the period of life where menopause trouble is disrupting their life.

In view of the above, it is apparent that there still is a great need for safe compositions with a consistent efficacy for the treatment of disorders relating to normal hormonal variations in women during fertile as well as, peri- and post-menopausal age.

A composition comprising an extract of combined pollen and pistils combined with a pollen grain extract, Royal Jelly and Vitamin E has been sold by Natumin Pharma AB, Kungs ängsvägen 27, 561 56 Huskvarna, Sweden, for the treatment of Pre-Menstrual Syndrome (PMS). Said composition was thought to be active against PMS disorders in general.

SUMMARY OF THE INVENTION

The present inventors during research work found out that the composition as disclosed in the application showed an unexpected advantageous effect on some disorders relating to normal variations in the hormone cycle of women. Other physiological parameters, such as heart rate and blood pressure, remain unaffected by the remedy.

The present inventors thus found an unexpected beneficial effect on some disorders relating to normal hormone variations of women of fertile, as well as peri- and post-menopausal age, obtained by the administering of a composition comprising, as active ingredients, a water- and/or fat-soluble cytosolic extract of pollen and optionally pistils, optionally in combination with Royal Jelly and Vitamin E. The invention is based on this discovery.

Said disorders in the peri- and post-menopausal women comprise menopausal hot flashes, tendencies of sweating, palpitations, muscle pains, headache, difficulties in passing water, stress incontinence, dysphoria, dry vaginal and mucous membranes, arthralgia, water retention, irritability, and variations in mood.

For women in fertile age the most unexpected and surprising effects were obtained on the disorders selected from irritability, dysphoria, bloatedness, edema, breast tension (mastalgia), weight changes, tension, headache, sleep disturbances, deteriorated overall wellbeing and interference in social and professional life.

The scope and preferred embodiments of the invention are as defined in the appended claims.

DETAILED DESCRIPTION OF THE INVENTION

The water-and/or fat-soluble cytosolic extract of pollen and optionally pistils preferably comprises an extract of pollen and pistils (PI 82) combined with an extract of pollen grain (GC FEM), as specified herein below. Both types of extract may be purchased from Allergon AB, Välingevägen 309, S-262 92 Ängelholm, Sweded, a Pharmacia company.

The pollens and pistils used for manufacturing of PI82 and GC FEM extracts are selected and harvested primarily from plants belonging to the grass family (Poaceae). During processing, treatment is performed on the pollen to open and remove the outer cell wall thereof as well as to minimize the risk of allergic pollen re-actions.

PI 82 is a cytosolic pollen-pistil extract rich in superoxide dismutase (SOD) mimics. The source of PI 82 is freshly harvested pollen grains and pistils. The pollen and pistils are allowed to react under very specific conditions. In the reaction, the process of fertilization is initiated between pollen and pistils, and the extract comprises the product thereof. Substances obtained in this reaction are SOD mimics, flavonoids, tannins and polyphenols. In vitro studies have shown that the extract has high superoxide dismutase activity and prevents the formation of free radicals. Experiences from double blind patient investigation show that PI 82 protects the body from the negative influence of free radicals. Furthermore, PI 82 improves the red cell function, thus improving oxygen perfusion to different tissues.

GC FEM is a water-soluble cytosolic extract from pollen. The cytoplasm content of the pollen contains, in addition to the above-mentioned substances, a high amount of carbohydrates and protein. Furthermore, carotenoids and traces of estrogen substances are found. GC FEM contains natural bioflavonoids, vitamins, enzymes and trace elements.

Royal Jelly is a product of the processing of various plant materials within the salivary glands of the worker honeybees. It is rich in pantothenic acid (also called Vitamin $B_5$), further vitamins and sterols. It is preferably included in the composition in lyophilized form, preferably concentrated by drying to a ratio of at least 1:3. Royal Jelly may be purchased from AB Montoil, Box 24150, S-104 51 Stockholm, Sweden.

As a source of Vitamin E, use is preferably made of Dry Vitamin E 50%, Type SD, from F. Hoffmann-La Roche Ltd., CH-4070 Basel, Switzerland. Preferably dl-alpha-tocopherol is used, but other forms might also be valuable.

Further, common drug processing compounds may be included, such as diluents, glidants, lubricants, disintegrants, flavoring and coloring agents well known to the man skilled in the art of pharmaceutical sciences.

The active ingredients may be included in formulations of any form, such as tablets, powders, granules, and tinctures. They also may be included in foodstuff of different origin, e.g. as functional food. Administration to the woman in need thereof may take place several times a day, such as 1–8 times daily, 1–6 times daily or 1–4 times daily.

A daily dosage may contain from 60 to 960 mg of PI 82; from 18 to 288 mg of GC FEM; and optionally from 2 to 48 mg of Royal Jelly. Vitamin E might be included in an amount of from 5 to 80 mg.

Preferably, a daily dosage may contain from 60 to 480 mg of PI 82; from 20 to 140 mg of GC FEM; optionally from 2 to 30 mg of Royal Jelly; and optionally from 5 to 60 mg/day Vitamin E.

More preferably, a daily dosage may contain from 60 to 360 mg of PI 82, 20 to 80 mg of GC FEM, and optionally from 2 to 15 mg of Royal Jelly and optionally from 10 to 40 mg of Vitamin E.

Most preferably, a daily dosage may contain 240 mg PI 82, 72 mg of GC FEM and optionally 12 mg of Royal Jelly and optionally 20 mg of Vitamin E.

It should be noted that, unless no statement to the contrary is made, all amounts of Royal Jelly quoted herein refer to freeze-died, i.e. lyophilized, Royal Jelly. The weight of Royal Jelly before freeze-drying is about at least three times higher, due to the water content of the same.

It furthermore should be noted that all the amounts of Vitamin E quoted herein refer to d-alpha-tocopherol, unless no statement to the contrary is made.

The remedy comprising the active ingredients should be administered to the woman in need thereof daily during at least one month, preferably at least two months. It may be administered in a single dose or in multiple doses.

Other excipients are included in amounts well known to any one skilled in the art of pharmaceutical sciences.

Test of the Effects on Disorders Relating to Normal Variations of the Sex Hormone Pattern of Women of Fertile Age A double-blind study was performed to investigate the efficacy and tolerability of the active composition in comparison to placebo in outpatients suffering from different disorders or affections relating to normal variations in the sex hormone pattern of women. Patients with depression and anxiety were excluded. The investigated disorders and affections were tension, irritability, dysphoria, weight change (kg), edema, swelling (bloating), breast tension, headache, sleep disturbances, deteriorated overall wellbeing as well as interference with social and professional life.

A 10-cm VAS (visual analogous scale) was used for all the investigated disorders except the weight gain, which was measured in kg.

The trial was performed on 32 women aged 27 to 54 years (mean 39.4 years), with regular menstrual cycles of 24 to 34 days. Criteria for admission were women aged 20 to 54 years with regular menses complaining of affections related to variations in the normal sex hormone pattern. 29 women completed the study.

After a pre-study screening, half of the patients (Group A) took 2 placebo tablets twice daily, starting on the first day after menstruation, and continued this treatment for two menstrual cycles, i.e. treatment period 1. The other half (Group B) followed the same regimen, but they were administered 2 tablets twice daily, each tablet comprising 120 mg of PI 82, 36 mg of GC FEM, 6 mg of Royal Jelly and 10 mg of dl-alpha-tocopheryl acetate. Thereafter, and without any "wash-out" period, each group crossed over to the other medication for another two menstrual cycles, i.e. to treatment period 2. Both groups started their medication periods at the same time. No formal rules for withdrawal, other than the patient's own wish to withdraw, was considered necessary. No dropouts due to protocol deviations were recorded.

Statistical Analysis

A non-parametric method (Wilcoxon signed-rank, matched pair analysis) was used for analysis of differences between treatment scores, on an intention to treat basis. A p-value of 0.05 or less was adopted as the acceptable significance level. With 29 patients available for evaluation, a day-to-day variation of 12%, a Type I error risk of 5%, and a Type II error risk of 10%, it would be possible to detect a score difference of 16%. To detect a possible "carry-over" effect, it was decided that a separate statistical analysis of Group A and B should also be performed (cf. Tables 13 and 14). An independent institution outside the clinic performed the statistical analysis.

Drug Formulations, Randomization and Blinding

The active composition and placebo tablets were formulated and packed to be indistinguishable for patients as well as for doctor and nurse. Treatments were allotted at random by computer generation for clusters of four individuals. The code list was generated and kept outside the clinic until the study had been completed. Drug formulations were packed and labeled for one month's treatment, and with a code number identifying the patient.

Results

Effects were analyzed as differences in various kinds of scores and in weight reduction for placebo and treatment with the disclosed composition, respectively.

Of the disorders and affections from the test protocol, evaluated with VAS by patients, the product significantly reduced four as compared to placebo, viz. irritability (p<0.05), dysphoria (p<0.02), feeling of being bloated (p<0.05), and edema (p<0.02). The reduction in scores amounted to 36%, 41%, 41% and 47% respectively. The reduced awareness of edema agrees well with the 57% reduction in gain in body weight. Tendencies of effects are also shown for breast tension and headache. The letters "ns" below means "not significant". A spillover effect might be obtained from the treatment with the active compound to the placebo test. According to later follow-up tests, reported in Tables 13 and 14, remarkably good effects were obtained.

Irritability Score

During the first cycle the irritability score (visual analogue scales 1–10) was 4.2 during placebo treatment as compared to 3.1 during treatment with the active composition. The corresponding figures for the second cycle was 4.4 for placebo and 2.8 for the active composition. The difference between placebo and the active composition was statistically significant between the two treatments during the second cycle, while there was a tendency of improvement during the first. The score was statistically significant lower during the second the active composition period compared to the first ($p<0.05$), and a carry-over effect was observed.

TABLE 1

Irritability score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 4.2 | 3.1 | 4.4 | 2.8 |
| Range | 0–9.4 | 0–9.5 | 0–9.3 | 0–9.5 |
| S.D. | 3.3 | 3.0 | 3.4 | 3.1 |
| p-value |  | ns |  | $p < 0.05$ |

Dysphoria Score

During the first cycle the dysphoria score (visual analogue scales 1–10) was 3.1 during placebo treatment as compared to 2.6 during the active composition treatment. The corresponding figures for the second cycle was 3.9 for placebo and 2.3 for the active composition. The difference between placebo and the active composition was statistically significant between the two treatments during the second cycle, while there was a tendency of improvement during the first.

TABLE 2

Dysphoria score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.1 | 2.6 | 3.9 | 2.3 |
| Range | 0–7.8 | 0–9.5 | 0–9.2 | 0–9.5 |
| S.D. | 2.7 | 3.1 | 3.1 | 2.9 |
| p-value |  | ns |  | $p < 0.02$ |

Bloating Score

During the first cycle the bloating score (visual analogue scales 1–10) was 3.9 during placebo treatment as compared to 2.4 during the active composition treatment. The corresponding figures for the second cycle was 3.7 for placebo and 2.2 for the active composition. The difference between placebo and the active composition was statistically significant between the two treatments for the first cycle and on the borderline on the second cycle (0.054). There was a significant carry-over effect.

TABLE 3

Bloating score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.9 | 2.4 | 3.7 | 2.2 |
| Range | 0–9.5 | 0–9.5 | 0–9.5 | 0–9.5 |
| S.D. | 3.0 | 2.9 | 3.6 | 2.9 |
| p-value | $p < 0.05$ |  | $p = 0.054$ |  |

Edema Score

During the first cycle the edema score (visual analogue scales 1–10) was 3.3 during placebo treatment as compared to 2.2 during the active composition treatment. The corresponding figures for the second cycle was 3.2 for placebo and 1.7 for the active composition. The difference between placebo and the active composition was statistically significant between the two treatments during the second cycle. A significant carry-over effect was found.

TABLE 4

Edema score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.3 | 2.2 | 3.2 | 1.7 |
| Range | 0–10 | 0–9.5 | 0–10 | 0–9.5 |
| S.D. | 3.4 | 3.1 | 3.6 | 2.7 |
| p-value |  | ns |  | $p < 0.02$ |

Breast Tension Score

During the first cycle the breast tension score (visual analogue scales 1–10) was 3.3 during placebo treatment as compared to 2.9 during treatment with the active composition. The corresponding figures for the second cycle was 3.5 for placebo and 2.5 for the active composition. The differences between placebo and the active composition were not statistically significant between the two treatments.

TABLE 5

Breast tension score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.3 | 2.9 | 3.5 | 2.5 |
| Range | 0–10 | 0–10 | 0–10 | 0–8.3 |
| S.D. | 3.4 | 3.2 | 3.8 | 2.9 |
| p-value |  | ns |  | ns |

Weight Increase

During the first cycle the patients weight increase was 1.2 kg during placebo treatment as compared to 1.0 during treatment with the active compound. The corresponding figures for the second cycle was 1.4 for placebo and 0.6 for the active compound. The difference between placebo and the active compound was statistically significant between the two treatments during the second cycle. It was a statistically significant difference between the first the active compound period and the second. A significant carry-over effect was found.

TABLE 6

Weight (kg) increase in connection with PMTS during treatment with Placebo and the active compound (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 1.2 | 1.0 | 1.4 | 0.6 |
| Range | 0–5.5 | 0–3 | 0–5 | 0–3 |
| S.D. | 1.3 | 1.0 | 1.3 | 0.8 |
| p-value |  | ns |  | p < 0.01 |

Tension Score

During the first cycle the tension score (visual analogue scales 1–10) was 3.4 during placebo treatment as compared to 2.6 during treatment with the active compound. The corresponding figures for the second cycle was 3.7 for placebo and 2.5 for the active compound. The difference between placebo and the active compound was not statistically significant between the two treatments during any of the cycles, even if it was a strong tendency of improvement during the second (p=0.060). There was a statistically significant carry-over effect between the periods.

TABLE 7

Tension score (VAS 0–10) during treatment with Placebo and the active compound (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.4 | 2.6 | 3.7 | 2.5 |
| Range | 0–8.2 | 0–9.5 | 0–9.2 | 0–9.5 |
| S.D. | 2.7 | 3.2 | 3.0 | 3.0 |
| p-value |  | ns |  | ns |

Headache Score

During the first cycle the headache score (visual analogue scales 1–10) was 3.7 during placebo treatment as compared to 2.1 during treatment with the active composition. The corresponding figures for the second cycle was 3.0 for placebo and 2.4 for the active composition. The differences between placebo and the active composition were not statistically significant between the two treatments.

TABLE 8

Headache score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 3.7 | 2.1 | 3.0 | 2.4 |
| Range | 0–10 | 0–8.9 | 0–9.5 | 0–9.5 |
| S.D. | 3.3 | 2.8 | 3.4 | 3.1 |
| p-value |  | ns |  | ns |

Sleep Disturbances Score

During the first cycle the sleep disturbances score (visual analogue scales 1–10) was 2.8 during placebo treatment as compared to 2.0 during treatment with the active composition. The corresponding figures for the second cycle was 3.1 for placebo and 2.5 for the active composition. The differences between placebo and the active composition were not statistically significant between the two treatments.

TABLE 9

Sleep disturbances score (VAS 0–10) during treatment with Placebo and the active composition (n = 29) at each menstrual cycle.

|  | Placebo 1st Cycle | Active 1st Cycle | Placebo 2nd Cycle | Active 2nd Cycle |
| --- | --- | --- | --- | --- |
| Mean | 2.8 | 2.0 | 3.1 | 2.5 |
| Range | 0–10 | 0–8.7 | 0–10 | 0–9.3 |
| S.D. | 3.3 | 3.1 | 3.6 | 3.3 |
| p-value |  | ns |  | ns |

Heart Rate

No statistically significant differences between placebo and the active composition were found between the two treatments.

TABLE 10

Heart rate after treatment with Placebo and the active composition (n = 29) after each menstrual cycle.

|  | Placebo 1st Cycle | Active 1st Cycle | Placebo 2nd Cycle | Active 2nd Cycle |
| --- | --- | --- | --- | --- |
| Mean | 74.2 | 76.3 | 75.4 | 77.6 |
| Range | 64–90 | 64–94 | 56–88 | 68–92 |
| S.D. | 6.7 | 8.5 | 8.1 | 6.5 |
| p-value |  | ns |  | ns |

Systolic Blood Pressure

No statistically significant differences between placebo and the active composition were found between the two treatments.

TABLE 11

Systolic blood pressure after treatment with Placebo and the active composition (n = 29) after each menstrual cycle.

|  | Placebo 1st Cycle | Active 1st Cycle | Placebo 2nd Cycle | Active 2nd Cycle |
| --- | --- | --- | --- | --- |
| Mean | 114.5 | 114.8 | 112.1 | 113.5 |
| Range | 90–135 | 90–150 | 95–125 | 90–130 |
| S.D. | 12.0 | 13.9 | 8.5 | 10.4 |
| p-value |  | ns |  | ns |

Diastolic Blood Pressure

No statistically significant differences between placebo and the active composition were found between the two treatments.

TABLE 12

Diastolic blood pressure after treatment with Placebo and the active composition (n = 29) after each menstrual cycle.

|  | Placebo 1st Cycle | Active 1st Cycle | Placebo 2nd Cycle | Active 2nd Cycle |
| --- | --- | --- | --- | --- |
| Mean | 77.4 | 77.1 | 78.1 | 79.4 |
| Range | 60–90 | 60–85 | 70–90 | 70–90 |
| S.D. | 6.4 | 7.0 | 5.3 | 5.9 |
| p-value |  | ns |  | ns |

The results of a further statistical analysis are presented in Tables 13 and 14. The analysis was performed in line with the Wilcoxon test performed above. In table 13 results are shown relating to the participants who obtained placebo during the first two treatment periods and the active composition during the two second treatment periods, in Table 14 the results relating to the opposite group are presented.

The treatment with the active composition shows an unexpected and remarkably better effect as compared to the placebo treatment.

product works for the individual patient. For one of the ingredients included in the active composition—PI 82—a similar observation has been made regarding the effect on

TABLE 13

Group A

| | Menstrual cycle no. | | | | | | | |
|---|---|---|---|---|---|---|---|---|
| | 1 | 2 | 3 | 4 | | | | |
| | | | Treatment | | | | | |
| | Placebo | Placebo | Active Comp. | Active Comp. | | P value matrix | | |
| Code | AP1 | AP2 | AF1 | AF2 | AP1 vs AP2 | AP2 vs AF1 | AF1 vs AF2 | AP2 vs AF2 |
| Tension | 4.1 +/− 2.9 | 4.2 +/− 3.3 | 1.7 +/− 2.8 | 1.2 +/− 2.4 | ns | 0.0134 | 0.0117 | 0.0012 |
| Irritability | 4.9 +/− 3.5 | 4.7 +/− 3.8 | 2.1 +/− 2.5 | 1.4 +/− 2.5 | ns | 0.0261 | 0.0020 | 0.0081 |
| Dysphoria | 3.2 +/− 2.4 | 4.7 +/− 3.1 | 1.6 +/− 2.7 | 1.4 +/− 2.3 | ns | 0.0107 | (0.0907) | 0.0024 |
| Weight change (kg) | 1.5 +/− 1.6 | 1.6 +/− 1.6 | 0.6 +/− 0.9 | 0.4 +/− 0.5 | ns | 0.0239 | ns | 0.0039 |
| Edema | 4.3 +/− 3.7 | 4.2 +/− 3.8 | 0.5 +/− 0.8 | 0.5 +/− 0.8 | ns | 0.0039 | ns | 0.0010 |
| Swelling (bloating) | 4.7 +/− 2.3 | 4.4 +/− 3.6 | 1.2 +/− 1.2 | 0.9 +/− 1.6 | ns | 0.0245 | ns | 0.0107 |
| Breast tension | 4.1 +/− 3.4 | 3.8 +/− 3.8 | 2.5 +/− 3.0 | 1.4 +/− 2.6 | ns | ns | 0.0195 | 0.0105 |
| Headache | 4.0 +/− 3.6 | 3.5 +/− 3.7 | 0.9 +/− 1.2 | 1.6 +/− 3.0 | ns | 0.0137 | ns | 0.0371 |
| Sleep disturbance | 4.5 +/− 3.6 | 5.0 +/− 3.9 | 2.2 +/− 3.1 | 2.6 +/− 3.6 | ns | 0.0266 | ns | 0.0081 |
| Overall wellbeing | 3.2 +/− 1.3 | 3.4 +/− 1.5 | 1.5 +/− 1.2 | 1.5 +/− 1.1 | ns | 0.0048 | ns | 0.0012 |
| Interf. social/prof. life | 3.7 +/− 2.7 | 3.7 +/− 3.3 | 1.2 +/− 1.6 | 0.8 +/− 1.8 | ns | 0.0093 | (0.0781) | 0.0034 |

TABLE 14

Group B

| | Menstrual cycle no. | | | | | | | |
|---|---|---|---|---|---|---|---|---|
| | 1 | 2 | 3 | 4 | | | | |
| | | | Treatment | | | | | |
| | Active comp. | Active comp. | Placebo | Placebo | | P value matrix | | |
| Code | BF1 | BF2 | BP1 | BP2 | BF1 vs BF2 | BF2 vs BP1 | BP1 vs BP2 | BF2 vs BF2 |
| Tension | 3.6 +/− 3.3 | 3.9 +/− 3.2 | 2.6 +/− 2.4 | 3.1 +/− 2.5 | ns | ns | ns | ns |
| Irritability | 4.3 +/− 3.1 | 4.3 +/− 3.2 | 3.5 +/− 2.9 | 4.1 +/− 2.9 | ns | ns | ns | ns |
| Dysphoria | 3.5 +/− 3.6 | 3.2 +/− 3.4 | 2.9 +/− 3.0 | 3.0 +/− 2.9 | ns | ns | ns | ns |
| Weight change (kg) | 1.4 +/− 1.0 | 0.8 +/− 1.0 | 0.8 +/− 0.8 | 1.1 +/− 0.9 | 0.0239 | ns | ns | ns |
| Edema | 4.1 +/− 3.7 | 2.9 +/− 3.4 | 2.4 +/− 2.9 | 2.1 +/− 3.0 | 0.0176 | ns | ns | ns |
| Swelling (bloating) | 3.7 +/− 3.4 | 3.6 +/− 3.6 | 3.1 +/− 3.1 | 3.1 +/− 3.6 | ns | ns | ns | ns |
| Breast tension | 3.4 +/− 3.4 | 3.6 +/− 3.1 | 2.5 +/− 3.3 | 3.3 +/− 4.1 | ns | ns | ns | ns |
| Headache | 3.4 +/− 3.5 | 3.2 +/− 3.1 | 3.4 +/− 3.0 | 2.5 +/− 3.2 | ns | ns | ns | ns |
| Sleep disturbances | 1.8 +/− 3.5 | 2.4 +/− 3.2 | 1.0 +/− 1.7 | 1.0 +/− 1.5 | ns | ns | ns | 0.0371 |
| Overall wellbeing | 2.8 +/− 1.4 | 2.8 +/− 1.4 | 2.6 +/− 1.4 | 2.6 +/− 1.4 | ns | ns | ns | ns |
| Interf. social/prof. life | 2.2 +/− 2.2 | 2.6 +/− 3.2 | 1.6 +/− 2.4 | 1.7 +/− 2.5 | ns | ns | ns | ns |

During placebo no adverse events were reported. During the first cycle of the active composition treatment three patients noted a shortened menstrual cycle and one patient reported dizziness. During the second cycle with the active composition 5 patients reported a shorter menstrual cycle than normal. Apart from these events the patients tolerated the active composition very well. The lack of severe adverse events is also obvious from Tables 10–12 above.

The results from these studies show that the active composition had a strong effect on tension, irritability, dysphoria, weight gain, edema, bloating, mastalgia, headache, sleep disturbances, overall wellbeing and interference in the social and professional life. The active composition was well tolerated by the patients.

It is interesting to note that the effect of the active composition was more pronounced during the second menstrual cycle compared to the first cycle of active treatment. This indicates that the treatment should be continued for at least two cycles before it should be evaluated whether the product works for the individual patient. For one of the ingredients included in the active composition—PI 82—a similar observation has been made regarding the effect on free radical formation. The onset of effect is seen first after a month treatment. Another reason for this may be that the effect of the active composition continues after having been withdrawn. The observed carry-over effect may indicate this. This effect may be one of the reasons why the efficacy of the active composition is not optimal during the first cycle, i.e. it may be that the onset of efficacy for the product is faster than the present data indicate. This is supported by the data from an open pilot study were the effects were as good during the first menstrual cycle as during the second.

The mode of action is with present scientific knowledge not known. As the product contains three different natural constituents, each with a theoretically contributing effect, the combination of these may be a reason for the observed effect. The constituents PI 82 and GC FEM contain SOD mimics such as flavonoids, tannins and polyphenols. These SOD mimics have an effect on free radical formation, which may be a factor involved in redistribution of fluids, including edema, seen under stress situation. An improved oxygen perfusion may also be a contributing effect.

Vitamin E is added to the composition as an active ingredient or as an antioxidant and stabilizer.

Test of the Effects on Disorders Relating to Normal Variations of the Sex Hormone Pattern of Women in the Peri- and Post-Menopause Test Mode Ten women with an average age of 50.8 (range from 46 to 55) years were recruited for this open trial. All of them had been diagnosed to suffer from climacteric disorders. The menstruation had ceased for 5 women while being irregular for 5. None of the women were subject to any hormone therapy.

Each of the women obtained one tablet comprising the active ingredients in an amount of 120.0 mg PI 82, 36.0 mg GC FEM, 6.0 mg Royal Jelly and 10.0 mg dl-alpha-tocopheryl acetate, twice daily, morning and evening. The treatment did not affect pulse, or systolic or diastolic blood pressure.

The investigated disorders, all relating to variations in the normal sex hormone pattern of women in the peri-and post-menopause, were menopausal hot flashes, tendencies of sweating, palpitations, sleep disorders, vertigo, muscle pains, headache, difficulties in passing water (pollakiuria), stress incontinence, dysphoria, dry-vaginal and mucous membranes, arthralgia, water retention (edema), irritability, and variations in mood.

Evaluation of the disorder was performed by use of a 10-cm VAS (visual analogous scale).

Low values express favorable results. All statistical calculations are Wilcoxon test for matched pairs, if not otherwise stated. The results, illustrating the impact of active compositions on different menopausal disorders, are compiled in Table 15.

TABLE 15

The impact of active compositions on different menopausal disorders Mean value (standard deviation).

| Menopausal disorders | Without treatment (cm) | Treatment by active comp. 1 month (cm) | Treatment by active comp. 2 months (cm) |
|---|---|---|---|
| Hot flushes | 3.08 (2.27) | 2.81 (2.03) | 1.33 (2.00)** |
| Sweating tendencies | 3.94 (2.29) | 2.75 (2.37) | 1.73 (2.54)* |
| Palpitations | 2.66 (2.74) | 1.88 (1.37) | 1.31 (1.66)# |
| Muscle pain | 3.40 (3.19) | 2.19 (1.42) | 2.08 (2.40)** |
| Headache | 3.77 (2.84) | 2.38 (2.20)*** | 2.53 (1.98)*** |
| Stress incontinence or frequent passing water (pollakiuria) | 1.73 (2.34) | 1.15 (1.44) | 0.72 (0.85)# |
| Dysphoria | 3.41 (2.05) | 2.16 (1.27)* | 1.60 (1.22)** |
| Dry vaginal and mucous membranes and/or pain during intercourse | 3.02 (2.88) | 1.36 (1.31)*** | 1.52 (2.32)*** |
| Joint pain | 3.94 (2.82) | 1.91 (1.03) | 1.48 (1.30)** |
| Mood | 3.05 (2.26) | 2.72 (1.90) | 1.73 (1.15) |
| Edema | 6.04 (2.53) | 4.48 (1.93)* | 3.28 (1.59)** |
| Energy loss | 4.99 (2.15) | 3.82 (1.60)* | 2.72 (2.21)*** |
| Irritability | 3.18 (2.55) | 2.20 (1.78)*** | 1.61 (1.24)* |
| Sleep disturbances | 4.28 (3.89) | 3.00 (3.07) | 2.87 (3.09) |
| Mood swings | 3.33 (2.16) | 2.31 (1.07) | 1.81 (1.63)# |
| Oversensitivity | 4.03 (2.06) | 2.70 (2.07)* | 2.01 (1.79)** |

# = borderline significance
* = $p < 0.05$
** = $p < 0.02$
*** = $p < 0.01$

Hot flushes: significant ($p<0.02$) after two months.
Sweating tendencies: significant ($p<0.05$) after two months.
Palpitations: more than 50% reduction (borderline significant).
Muscle pains: significant ($p<0.02$) after one month and borderline after two months.
Headache: highly significant ($p<0.01$) after one and two months.
Stress incontinence and/or pollakiuria: reduction of about 60%, borderline significant.
Dysphoria: significant after one and two months ($p<0.05$ and $p<0.02$).
Dry vaginal or mucous membranes and/or pain during intercourse: significant after one and two months ($p<0.01$ and $p<0.01$)>50% reduction.
Joint pain: significant after two months ($p<0.02$)
Mood: not significant, however a favorable change of about 40% is obvious.
Edema/water retention: reduction of more than 50%, significant after one and two months ($p<0.05$ and $p<0.02$).
Energy loss: marked enhancement, significant after one and two months ($p<0.05$ and $p<0.01$).
Irritability: reduced by 50% ($p<0.01$ and $p<0.05$).
Sleep disturbances show a tendency of effect but is not significant.
Mood swings: borderline significant after two months.
Oversensitivity: significantly better after one and two months ($p<0.05$ and $p<0.02$).

If all VAS scores were added to a common "overall well-being score" a clearly positive effect is shown for 8 of 10 participants, only two were unchanged. Thus, the improvement is significant ($p<0.02$).

At a direct inquiry of all ten participants whether they have had any advantages or use of the treatment, 6 of them clearly said, "yes" while four answered "don't know" ($p<0.05$, Chi square).

EXAMPLE

Below is given an Example of a tablet used according to the invention.

| Active ingredients: | |
|---|---|
| PI 82 (pollen-pistil extract) | 120.0 mg |
| GC FEM (pollen extract) | 36.0 mg |
| Secondary ingredients: | |
| ROYAL JELLY (freeze dried) | 6.0 mg |
| VITAMIN E 50% | 20.0 mg |
| Other ingredients: | |
| icrocrystalline cellulose | 87.0 mg |
| Dicalcium phosphate | 87.0 mg |
| Magnesium stearate | 4.0 mg |
| Uncoated tablet weight | 360.0 mg |
| Coating: | |
| Shellac | approx. 2.64 mg |
| Talc | approx. 0.36 mg |
| Total weight | approx. 363.0 mg |

What is claimed is:

1. A method treatment of disorders related to normal hormonal variations in women during fertile, pen- and post-menopausal age, by administration of a composition comprising, as active ingredient, one or more water and/or fat-soluble cytosolic extract of pollen and optionally pistils, optionally combined with Royal Jelly and Vitamin E.

2. The method according to claim 1 wherein the water- and/or fat-soluble cytosolic extract is a combination of a first extract of pollen and pistils, and a second extract of pollen.

3. The method according to claim 2, wherein the first extract of pollen and pistils is PI 82 and the second extract of pollen is GC FEM.

4. The method according to claim 3 wherein the composition is administered in a daily dosage from 60 to 960 mg of PI 82, 18 to 288 mg of GC FEM, and optionally 2 to 48 mg of Royal Jelly D and 5 to 80 mg of Vitamin E.

5. The method of claim 4, wherein the daily dosage of the composition is administered in a single dose or in multiple subdoses, 2–8 times daily.

6. The method according to claim 3 wherein the composition is administered in a daily dosage of from 60 to 480 mg of PI 82, 20 to 140 mg of GC FEM, and optionally 2 to 30 mg of Royal Jelly and 5 to 60 mg of Vitamin E.

7. The method of claim 6, wherein the daily dosage of the composition is administered in a single dose or in multiple subdoses, 2–8 times daily.

8. The method according to claim 3 wherein the composition is administered in a daily dosage of from 60 to 360 mg of PI 82, 20 to 80 mg of GC FEM, and optionally 2 to 15 mg of Royal Jelly and 10 to 40 mg of Vitamin E.

9. The method of claim 8, wherein the daily dosage of the composition is administered in a single dose or in multiple subdoses, 2–8 times daily.

10. The method according to claim 3 wherein the composition is administered in a daily dosage of 240 mg PI 82, 72 mg of GC FEM, and optionally 12 mg of Royal Jelly and 20 mg of Vitamin E.

11. The method according to claim 1, wherein the composition is administered in a single dose or in multiple subdoses, 2–8 times daily.

12. The method according to claim 1, wherein the disorders relating to normal hormonal variations in women during fertile, peri- and post menopausal age are selected from the group consisting of menopausal hot flashes, tendencies of sweating, palpitations, muscle pains, headache, stress incontinence, pollakiuria, dysphoria, dry vaginal and mucous membranes, arthralgia, water retention, irritability, oversensitivity, and variations in mood.

13. The method according to claim 1, wherein one of the disorders treated is irritability of women in the fertile age.

14. The method according to claim 1, wherein one of the disorders treated is dysphoria of women in the fertile age.

15. The method according to claim 1, wherein one of the disorders treated is bloating of women in the fertile age.

16. The method according to claim 1, wherein one of the disorders treated is edema of women in fertile age.

17. The method according to claim 1, wherein one of the disorders treated is mastalgia of women in the fertile age.

18. The method according to claim 1, wherein one of the disorders treated is weight gain of women in the fertile age.

19. The method according to claim 1, wherein one of the disorders treated is tension of women in the fertile age.

20. The method according to claim 1, wherein one of the disorders treated is headache of women in the fertile age.

* * * * *

UNITED STATES PATENT AND TRADEMARK OFFICE
CERTIFICATE OF CORRECTION

PATENT NO.    : 6,669,967 B2
DATED         : December 30, 2003
INVENTOR(S)   : Winter et al.

It is certified that error appears in the above-identified patent and that said Letters Patent is hereby corrected as shown below:

<u>Column 12,</u>
Line 56, delete "pen-" and insert therefor -- peri- --.

Signed and Sealed this

Ninth Day of March, 2004

JON W. DUDAS
*Acting Director of the United States Patent and Trademark Office*